United States Patent [19]

Bargiotti et al.

[11] Patent Number: 5,304,687
[45] Date of Patent: Apr. 19, 1994

[54] MORPHOLINYL DERIVATIVES OF DOXORUBICIN AND PROCESS FOR THEIR PREPARATION

[75] Inventors: Alberto Bargiotti; Maria Grandi; Antonino Suarato, all of Milan; Daniela Faiardi, Pavia, all of Italy

[73] Assignee: Farmitalia Carlo Erba S.R.L., Milan, Italy

[21] Appl. No.: 3,684

[22] Filed: Jan. 13, 1993

Related U.S. Application Data

[63] Continuation of Ser. No. 741,539, Aug. 14, 1991, abandoned.

[30] Foreign Application Priority Data

Dec. 19, 1989 [GB] United Kingdom ............... 8928654
Apr. 3, 1990 [GB] United Kingdom ............... 9007513

[51] Int. Cl.$^5$ .................. C07C 43/313; C07C 43/30
[52] U.S. Cl. ................................. 568/604; 568/591
[58] Field of Search ........................ 568/604, 591

[56] References Cited

U.S. PATENT DOCUMENTS 4,374,980  2/1983  Umezawa et al. ................ 536/64
4,672,057  6/1987  Bargiotte et al. ............... 536/64

FOREIGN PATENT DOCUMENTS 188293   7/1986  European Pat. Off. .
3287739  11/1988  Japan .
479753   4/1976  U.S.S.R. .
2172594  9/1986  United Kingdom .

Primary Examiner—Werren B. Lone
Attorney, Agent, or Firm—Oblon, Spivak, McClelland, Maier & Neustadt

[57] ABSTRACT

Morpholinyl derivatives of doxorubicin having the general formula A:

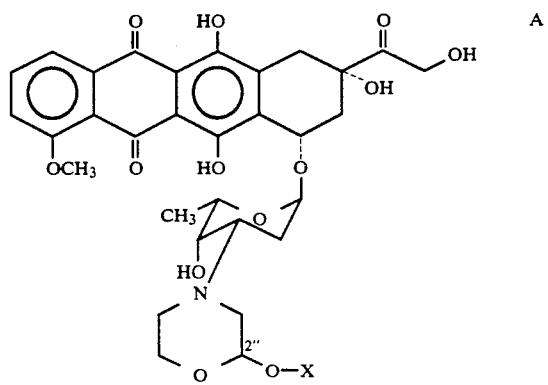

in which X represents a linear or branched $C_2$-$C_6$ alkyl group or a benzyl group —$CH_2C_6H_5$ and which have (S) or (R) configuration at carbon atom C-2" of the morpholino ring, are antitumor agents.

2 Claims, No Drawings

MORPHOLINYL DERIVATIVES OF DOXORUBICIN AND PROCESS FOR THEIR PREPARATION

This application is a continuation of application Ser. No. 07/741,539, filed on Aug. 14, 1991, now abandoned.

The invention relates to anthracycline glycosides, to processes for their preparation and to pharmaceutical compositions containing them.

The invention provides new anthracycline glycosides of general formula A in which the 3'-nitrogen atom is enclosed in a 2-alkoxy-4-morpholinyl ring:

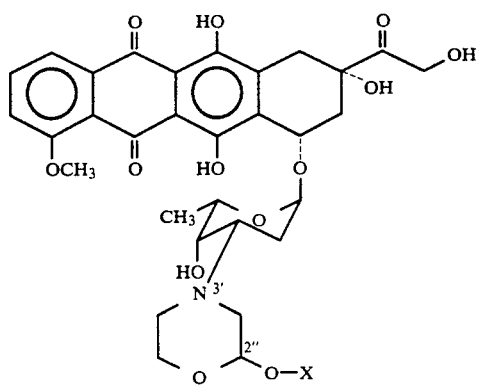

in which X represents a linear or branched $C_1-C_6$ alkyl group or a benzyl residue $-CH_2C_6H_5$ and which has a (S) or (R) configuration at the 2''-carbon atom, and pharmaceutically acceptable acid addition salts thereof. The preferred salt is the hydrochloride salt.

Morpholino-anthracyclines are well known compounds endowed with promising antitumor activity on experimental murine tumors [see: E. W. Acton in Bioactive Molecules, 55–101, vol 6, Edited by J. W. Lown, Elveiser 1988]. Among these, 2-methoxy-4-morpholinyl anthracyclines ($X=OCH_3$) have been already claimed in our patent U.S. Pat. No. 4,672,057. These compounds were prepared through a reductive-alkylating process using a chiral-dihaldehyde. In the present invention, on the other hand, the substituted morpholinyl rings are prepared through bis-alkylation of the 3'-amino group of anthracyclines with novel chiral 1,5-diiodo-2-alkoxy or -benzyloxy derivatives that are within the scope of the invention.

The preferred anthracycline glycosides of general formula A include:

A1: 3'-deamino-3'-(2''(S)-benzyloxy-4''-morpholinyl)-doxorubicin ($X=CH_2C_6H_5$),
A2: 3'-deamino-3'-(2''(S)-ethoxy-4''-morpholinyl)-doxorubicin ($X=C_2H_5$),
A3: 3'-deamino-3'-(2''(R)-isopropyloxy-4''-morpholinyl)-doxorubicin ($X=CH(CH_3)_2$),
A4: 3'-deamino-3'-(2''(S)-methoxy-4''-morpholinyl)-doxorubicin ($X=CH_3$), and
A5: 3'-deamino-3'-(2''(R)-methoxy-4''-morpholinyl)-doxorubicin ($X=CH_3$).

and their hydrochloride salts. The compounds may have a (S) or (R) configuration at carbon atom C-2'' of the morpholino ring.

The new anthracycline glycoside antibiotics of the invention, i.e. those of general formula A, are prepared by the formation of a substituted morpholinyl ring at C-3' on the sugar moiety of the antitumor anthracycline glycoside doxorubicin (B):

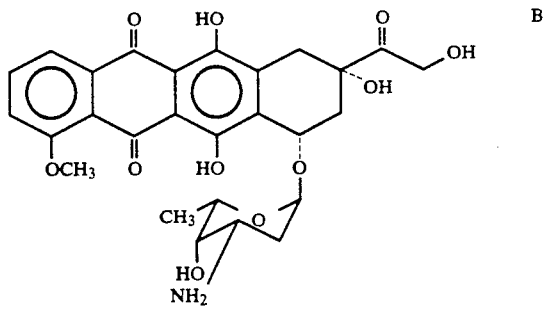

The present invention therefore provides a process for the preparation of an anthracycline glycoside of formula A or a pharmaceutically acceptable acid addition salt thereof, which process comprises:

(i) reacting doxorubicin or an acid addition salt thereof, for example the hydrochloride salt, with a diiodo compound of general formula C:

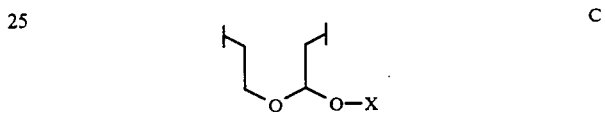

wherein X is as defined above; and (ii) if desired, converting the anthracycline glycoside of formula A thus obtained into a pharmaceutically acceptable acid addition salt thereof.

The alkylation of the C-3' amino group of doxorubicin or the doxorubicin salt is typically performed in step (i) in a polar aprotic solvent and in the presence of a dry organic base such as triethylamine. Reaction is generally carried out at room temperature from eight to twenty four hours. The carbon atom C-2 bearing the $-OX$ group in the diiodo compound may have a (S) or (R) configuration. In a preferred embodiment, doxorubicin or its hydrochloride, dissolved in a polar aprotic solvent is reacted, at room temperature and in the presence of a dry organic base, with the diiodo compound of general formula C to give the corresponding morpholinyl doxorubicin derivative of formula A which, after purification on a silica gel column using as eluting system methylene chloride-methanol (97:5 v/v), is isolated, by treatment with methanolic anhydrous hydrogen chloride, as its hydrochloride. A pure 2''(R)-[($C_1$–$C_6$) alkoxy or benzyloxy]-anthracycline glycoside of formula A or salt thereof, or a pure 2''(S)-[($C_1$–$C_6$)alkoxy or benzyloxy]-anthracycline glycoside of formula A or salt thereof, may therefore be provided according to the present invention.

The invention also provides a process for the preparation of optically pure diiodo compounds C, starting from sugar precursors such as the compound of general formula S derived from L-arabinose:

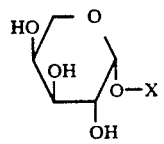

wherein X is as defined above. This process comprises:

(a) subjecting to periodate oxidation a compound of formula $S^1$:

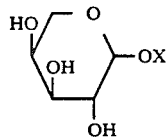

wherein X is as defined above;

(b) reducing the thus-obtained dialdehyde derivative of formula $D^1$:

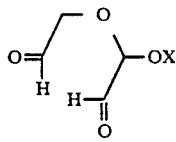

wherein X is as defined above;

(c) sulfonating the thus-obtained dihydroxy derivative of formula $E^1$:

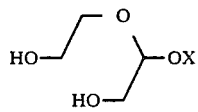

wherein X is as defined above; and (d) iodinating the sulfonated derivative thus obtained.

In order to prepare the diiodo compounds C, 1-substituted sugars $S^1$, prepared following standard procedures described in "Methods on Carbohydrate Chemistry" Acad. Press., Vol 1, (1962), are first transformed into dialdehyde derivatives $D^1$. Generally, D- or L-arabinose is employed as a starting material. This is reacted with an alcohol X-OH thereby to form the compound of formula $S^1$. The dialdehyde derivatives can be obtained by using periodate oxidation in water, then reduced to 1,5-dihydroxy-2-alkoxy or -benzyloxy-3-oxa-pentane $E^1$ by using reducing agents such as sodium borohydride or sodium cyanoborohydride at pH 6.5 in a mixture of water and methanol.

The resultant dihydro compounds $E^1$ are sulfonated at the 1- and 5-hydroxyl groups, typically by using p-toluensulfonyl chloride in pyridine at 4° C. to give the sulfonyl esters of formula F from which the diiodo derivatives C are obtained upon treatment with sodium or potassium iodide in aprotic solvent such as methylethylketone at 85° C. from one to two days. The sequence of these reactions do not affect the chirality at C-2 of the diiodo derivatives C which is the same of the starting sugars S.

A preferred embodiment of a process according to the invention is illustrated by the following reaction Scheme:

Reaction Scheme

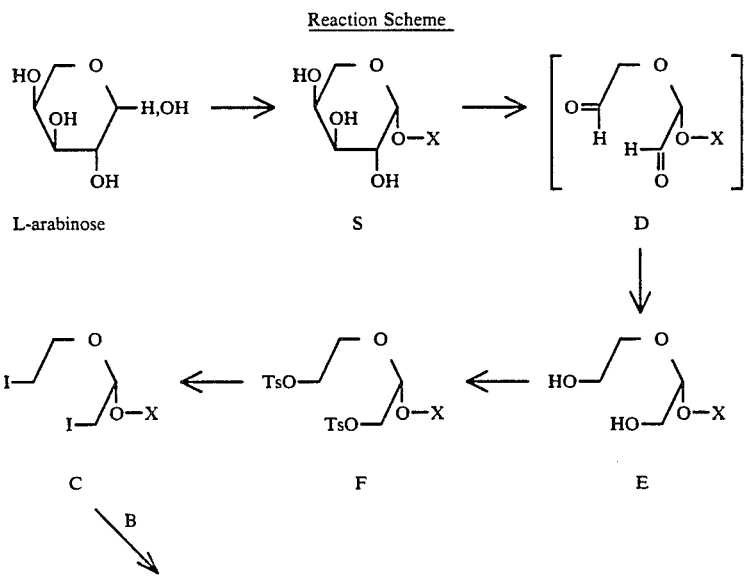

Reaction Scheme

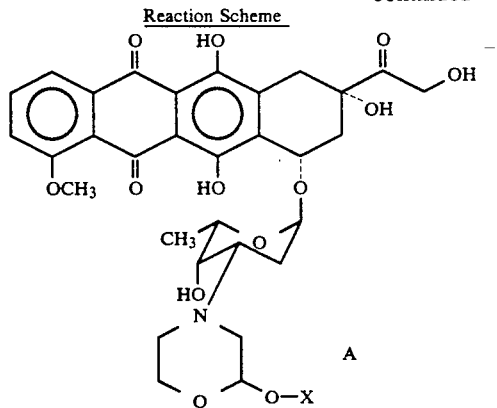

Ts = O₂S—C₆H₄pCH₃

The present invention also provides pharmaceutical compositions comprising a pharmaceutically acceptable carrier or diluent and, as active ingredient, an anthracycline glycoside of formula A or a pharmaceutically acceptable acid addition salt thereof. Conventional carriers or diluents may be used. The composition may be formulated and administered, for example intravenously, in conventional manner.

The anthracycline glycosides of formula A and pharmaceutically acceptable acid addition salts thereof are antitumour agents. They may be used to treat a patient with a tumour by administration of a therapeutically effective amount thereof. The compounds can be used to inhibit the growth of a tumour and are non-toxic at therapeutic doses.

The following Examples illustrate the invention.

EXAMPLE 1

Preparation of 1,5-di(p-toluensulphonyl)oxy-2(s)-benzyloxy-3-oxa-pentane (F1)

L-arabinose (3 g, 0.022 mole) and benzyl alcohol (15 ml) were heated under stirring in presence of Dowex 50Wx2 (2 g) in acidic form. After four hours, the mixture was cooled and filtered. The solvent was removed under reduced pressure and 1-benzyl-β-L-arabinopyranoside (S1, 3.5 g) was recovered from acetone. TLC on Kieselgel Plate F$_{254}$ (Merck), eluting system methylene chloride/methanol/water (120/20/2 by volume) Rf=0.47. [α]$_D$= +215° (c=1% water).

1-benzyl-β-L-arabinopyranoside (S1, 3.48 g, 0.0145 mole) was dissolved in water (100 ml) and treated with sodium periodate (5.6 g, 0.026 mole) at 0° C. for two hours. Then barium chloride was added and the mixture was brought to pH 7 with barium carbonate, filtered off and washed with water. The aqueous solution was concentrated under reduced pressure to a syrup and extracted with acetonitrile (50 ml). The organic phase was diluted with a mixture of methanol (20 ml) and water (10 ml) and treated with sodium cyanoborohydride (0.3 g) dissolved in water (5 ml). After 15 minutes the mixture was brought to pH 7 by adding Dowex 50Wx2 and filtered. The solvents were removed under reduced pressure to give 1,5-dihydroxy-2(S)-benzyloxy-3-oxa-pentane (E1, 2.6 g, yield 85%). TLC on Kieselgel Plate F$_{254}$ (Merck), eluting system methylene chloride/methanol (10/1 by volume) Rur: Rf=0.28. Compound E1 (2.6 g) was dissolved in dry pyridine and added with p-toluensulfonylchloride (6.67 g). The mixture was kept at 0° C. overnight, then poured into ice-water and extracted with methylene chloride. The organic phase was washed with water, separated off, dryied over anhydrous sodium sulphate and filtered off. The solvent was removed under reduced pressure to afford 1,5-di(p-toluensulphonyl)oxy-2(S)-benzyloxy-3-oxa-pentane (F1, 4.3 g, yield 68%). TLC on Kieselgel Plate F$_{254}$ (Merck), eluting system methylene chloride/acetone (98/2 by volume) R$_f$=0.55

¹HNMR (CDCl₃, 400 MHz) δ: 2.42 (s, 6H, two CH₃Ts); 3.65, 3.69 (two dt, J=4.7, 11.7 Hz, 2H, TsOCH₂CH₂O); 3.94 (two, dd, J=5.3, 10.5 Hz, 2H, OCH—C$\underline{H_2}$—OTs); 4.08 (t, J=4.7 Hz, 2H, Ts—O—C$\underline{H_2}$CH₂—O); 4.46, 4.56 (two, d, J=11.7 Hz, 2H, OC$\underline{H_2}$—Ph); 4.72 (t, J=5.3 Hz, 1H, O—C$\underline{H}$—CH₂—OTs); 7.2–7.8 (m, 13H, aromatics).

EXAMPLE 2

Preparation of 1,5-diiodo-2(S)-benzyloxy-3-oxa-pentane (C1)

Compound F1 (4.3 g, 8.3 mmole), prepared as described in Example 1, was dissolved in methylethylketone (50 ml) and added with sodium iodide (7.4 g, 49 mmole). The mixture was kept at 95° C. for twenty four hours. After that, the solvent was removed under reduced pressure and the residue was extracted with n-hexane. The organic phase was concentrated to a syrup to give the title compound C1 (3.5 g, yield 90%). TLC on Kieselgel Plate F$_{254}$ (Merck), eluting system n-hexane/ethyl acetate (10/0.5 by volume) R$_f$=0.34

¹HNMR (CDCl₃, 400 MHz) δ: 3.27 (t, J=6.8 Hz, 2H, J—CH₂CH₂—O); 3.30 (d, J=5.5 Hz, 2H, O—CH—C$\underline{H}$₂—J); 3.84 (m, 2H, J—CH₂CH₂—O); 4.63, 4.74 (two d, J=11.7 Hz, 2H, O—CH₂Ph); 4.81 (t, J=5.5 Hz, 1H, O—C$\underline{H}$—CH₂—J); 7.3–7.5 (m, 5H, aromatics).

EXAMPLE 3

Preparation of 3'-deamino-3'[2(S)-benzyloxy-4-morpholinyl]doxorubicin (A1)

To a solution of doxorubicin hydrochloride (0.5 g, 0.86 mmole) in dry dimethylformamide (20 ml) was added 1,5-diiodo-2(S)-benzyloxy-3-oxa-pentane (C1, 3.5 g, 7.54 mmole) and dry triethylamine (3.6 ml, 2.6 mmole). The mixture was kept at room temperature for 36 hours, then was poured in water and extracted with methylene chloride. After standard work-up, the crude product was purified on silicic acid column using as eluting system a mixture of methylene chloride/methanol (97/5 by volume), to give, after treatment with methanolic anhydrous hydrogen chloride, the title compound A1 (0.3 g, yield 46%) as hydrochloride salt.

TLC on Kieselgel Plate $F_{254}$ (Merck), eluting system methylene chloride/methanol (10/1 by volume) $R_f=0.6$.

FD-MS: m/e 756 (M+)

$^1$HNMR of free base (CDCl$_3$, 200 MHz) δ: 1.37 (d, J=6.6 Hz, 3H, 5'—CH$_3$); 1.76 (m, 2H, 2'—CH$_2$); 2.14 (dd, J=3.9, 14.8 Hz, 1H, 8ax-H); 2.2-2.7 (m, 6H, CH$_2$—N—CH$_2$, 8eq-H, 3'-H); 3.00 (d, J=18.8 Hz, 1H, 10ax-H); 3.55, 4.00 (two m, 2H, O—CH$_2$CH$_2$N); 3.68 (s, 1H, 4'-H); 3.94 (q, J=6.6 Hz, 1H, 5'-H); 4.08 (s, 3H, OCH$_3$); 4.51, 4.77 (two d, J=12.1 Hz, 2H, OCH$_2$Ph); 4.65 (dd, J=2.6, 4.0 Hz, 1H, OCH(OCH$_2$Ph)CH$_2$N); 4.71 (s, 1H, COCH$_2$OH); 5.28 (dd, J=2.4, 3.8 Hz, 1H, 7-H); 5.54 (m, 1H, 1'-H); 7.2-8.1 (m, 8H, aromatic H's); 13.22 (s, 1H, 11-OH); 13.95 (s, 1H, 6-OH).

EXAMPLE 4

Preparation of 1,5-diiodo-2(S)-ethoxy-3-oxa-pentane (C2)

The title compound C2 was prepared starting from L-arabinose (3 g) following sequential reactions as described in Example 1 and Example 2.

1-ethyl-α-L-arabinopyranoside (S2): [α]$_D$=+233.5° (c=1% water) 1,5-dihydroxy-2(S)-ethoxy-3-oxa-pentane (E2): TLC on Kieselgel Plate $F_{254}$ (Merck) eluting system methylene chloride/methanol (10/1 by volume) $R_f=0.33$.

1,5-di(p-toluensulphonyl)oxy-2(S)-ethoxy-3-oxa-pentane (F2): TLC on Kieselgel Plate $F_{254}$ (Merck), eluting system methylene chloride/acetone (98/2 by volume) $R_f=0.56$ $^1$HNMR (CDCl$_3$, 200 MHz) δ: 1.11 (t, J=7.0 Hz, 3H, OCH$_2$CH$_3$); 2.43 (s, 6H, two CH$_3$—Ts); 3.44, 3.58 (two dq, J=7.0, 9.4 Hz, 2H, OCH$_2$CH$_3$); 3.68 (m, 2H, O—CH$_2$—CH$_2$—OTs); 3.89 (d, J=5.4, 2H, O—CH—CH$_2$—OTs); 4.10 (t, J=4.8 Hz, 2H, OCH$_2$—CH$_2$OTs); 4.61 (t, J=5.4 Hz, 1H, O—CH—CH$_2$OTs); 7.3-7.8 (m, 8H, aromatic H's).

1,5-diiodo-2(S)-ethoxy-3-oxa-pentane (C2): TLC on Kieselgel Plate $F_{254}$ (Merck), eluting system n-hexane/ethyl acetate (10/0.5 by volume) $R_f=0.37$ $^1$HNMR (CDCl$_3$, 200 MHz) δ: 1.24 (t, 7.0 Hz, 3H, OCH$_2$CH$_3$); 3.23 (d, J=5.6 Hz, 2H, J—CH$_2$CH—O); 3.27 (t, J=6.8 Hz, 2H, J—CH$_2$CH$_2$—O); 3.58, 3.77 (two dq, J=7.0, 9.3 Hz, 2H, OCH$_2$CH$_3$); 3.78, 3.87 (two dt, J=6.8, 10.6 Hz, 2H, J—CH$_2$CH$_2$—O); 4.70 (t, J=5.6 Hz, 1H, O—CH—CH$_2$—J).

EXAMPLE 5

Preparation of 3'-deamino-3'[2(S)-ethoxy-4-morpholinyl]doxorubicin (A2)

Doxorubicin hydrochloride (0.5 g) was reacted with compound C2 (3 g) following the same procedure reported in Example 3 to give the title compound A2 (0.28 g) as hydrochloride salt. TLC on Kieselgel Plate $F_{254}$ (Merck), eluting system methylene chloride/methanol (10/1 by volume) $R_f=0.58$ FD-MS: m/e 694 (M+)

$^1$HNMR as free base (CDCl$_3$, 200 MHz) δ: 1.16 (t,J=7.0 Hz, 3H, OCH$_2$CH$_3$); 1.36 (d, J=6.4 Hz, 3H, 5'-CH$_3$); 1.7-1.8 (m, 2H, 2'-CH$_2$); 2.16 (dd, J=4.1, 14.7 Hz, 1H, 8ax-H); 2.3-2.6 (m, 6H, CH$_2$—N—CH$_2$); 8eq-H, 3'-H); 3.02 (d, J=18.8 Hz, 1H, 10ax-H); 3.26 (dd, 1.9, 18.8 Hz, 1H, 10eq-H); 3.46, 3.78 (two dq, J=7.0, 9.8 Hz, 2H, OCH$_2$CH$_3$); 3.53, 3.93 (two m, 2H, OCH$_2$CH$_2$N); 3.68 (s, 1H, 4'-H); 3.93 (q, J=6.4 Hz, 1H, 5'-H); 4.08 (s, 3H, OCH$_3$); 4.56 (dd, J=2.3, 4.7 Hz, 1H, OCH(OCH$_2$CH$_3$)CH$_2$N); 4.72 (s, 1H, 9-OH); 4.74 (s, 2H, COCH$_2$OH); 5.30 (m, 1H, 7-H); 5.55 (m, 1H, 1'-H); 7.3-8.1 (m, 3H, aromatic H's); 13.25 (s, 1H, 11-OH); 13.97 (s, 1H, 6-OH)

EXAMPLE 6

Preparation of 1,5-diiodo-2(R)-isopropyloxy-3-oxa-pentane (C3)

The title compound C3 was prepared starting from L-arabinose (3 g) following sequential reactions as described in Example 1 and Example 2.

1-isopropyl-β-L-arabinopyranoside (S3): [α]$_D$=+225° (water) 1,5-dihydroxy-2(R)-isopropyloxy-3-oxa-pentane (E3):

TLC on Kieselgel Plate $F_{254}$ (Merck), eluting system methylene chloride/methanol (10/1 by volume) $R_f=0.36$ 1,5-di(p-toluensulphonyl)oxy-2(R)-isopropyloxy-3-oxa-pentane (F3 TLC on Kieselgel Plate $F_{254}$ (Merck), eluting system methylene chloride/acetone (98/2 by volume) $R_f=0.55$ $^1$HNMR (CDCl$_3$, 200 MHz) δ: 1.05, 1.10 (two d, J=6.2 Hz, 6H, CH(CH$_3$)$_2$); 2.42 two s, 6H, CH$_3$-Ts); 3.64 (two m, 2H, Ts—O—CH$_2$CH$_2$—O); 3.76 (m, 1H, CH(CH$_3$)$_2$); 3.84 (m, 2H, O—CH—CH$_2$—OTs); 4.08 (t, J=5.6 Hz, 2H, Ts—O—CH$_2$CH$_2$—O); 7.3-7.8 (m, 8H, aromatic H's).

1.5-diiodo-2(R)-isopropyloxy-3-oxa-pentane (C3)

TLC on Kieselgel Plate $F_{254}$ (Merck), eluting system n-hexane/ethyl acetate (10/0.5 by volume) $R_f=0.40$ $^1$HNMR (CDCl$_3$, 200 MHz) δ: 1.20, 1.22 (two d, J=6.4 Hz, 6H, CH(CH$_3$)$_2$); 3.24 (d, J=5.6 Hz, 2H, O—CH—CH$_2$—J); 3.28 (t, J=6.7 Hz, 2H, J—CH$_2$CH$_2$—O); 3.6-3.8 (m, 2H, J—CH$_2$CH$_2$—O); 3.94 (m, 1H, CH(CH$_3$)$_2$); 4.76 (t, J=5.6 Hz, 1H, O—CH—CH$_2$—J).

EXAMPLE 7

Preparation of 3'-deamino-3'[2(R)-isopropyloxyl-4-morpholinyl] doxorubicin (A3)

Doxorubicin hydrochloride (0.5 g) was reacted with compound C3 (3.2 g) following the same procedure reported in Example 3 to give the title compound A3 (0.21 g) as hydrochloride salt.

TLC on Kieselgel Plate $F_{254}$ (Merck), eluting system methylene chloride/methanol (10/1 by volume) $R_f=0.55$ FD-MS: m/e 708 (M+)

$^1$HNMR as free base (CDCl$_3$, 200 MHz) δ: 1.09, 1.16 (two d, J=6.0 Hz, 6H, CH(CH$_3$)$_2$); 1.36 (d, J=6.6 Hz, 3H, 5'-CH$_3$); 1.80 (m, 2H, 2'-CH$_2$); 2.15 (dd, J=4.0, 14.9 Hz, 1H, 8ax-H); 2.3-2.8 (m, 6H, CH$_2$NCH$_2$, 8eq-H, 3'-H); 2.97 (d, J=18.8 Hz, 1H, 10ax-H); 3.26 (d, J=18.8 Hz, 1H, 10eq-H); 3.54 (m, 1H, O—CH(H)CH$_2$N); 3.74 (s, 1H, 4'-H); 3.81-4.1 (m, 3H, OCH(H)CH$_2$N, 5'-H, OCH(CH$_3$)$_2$); 4.08 (s, 3H, OCH$_3$); 4.66 (s, 1H, 9-OH); 4.68 (dd, J=2.2, 4.9 Hz, 1H, OCH[OCH(CH$_3$)$_2$]CH$_2$N); 4.75 (s, 2H, COCH$_2$OH); 5.28 (m, 1H, 7-H); 5.55 (m, 1H, 1'-H); 7.3-7.8 (m, 3H, aromatic H's); 13.24 (s, 1H, 11-OH); 13.97 (s, 1H, 6-OH).

EXAMPLE 8

1,5-dihydroxy-2(S)-methoxy-3-oxa-pentane (E4)

1,5-dioxo-2(S)-methoxy-3-oxa-pentane (D4) (1.5 g, 11 mmole), prepared as described in "Methods on Carbohydrate Chemistry" Acad. Press., Vol. 1, 445, (1962), was dissolved in a mixture of water (10 ml) and methanol (10 ml) and treated with sodiumborohydride (0.1 g) dissolved in water (2 ml). After 20 minutes the solution was brought to pH 7 with an acidic resin Dowex 50WX2, filtered off and the solvent was removed under reduced pressure to give 1.4 g (Yield 93%) of the title compound. TLC on Kieselgel Plate $F_{254}$ (Merck), eluting system methylene chloride:methanol (10:1 by volume) brown spot at $R_f = 0.24$ after heating the TLC plate previously sprayed with sulforic acid.

$^1$HNMR (200 MHz, DMSO-$d_6$) δ: 3.26 (s, 3H, OCH$_3$); 3.4–3.6 (m, 6H, —CH$_2$—CH$_2$—O—CH—CH$_2$—); 4.37 (t, J=5.4 Hz, 1H, O—CH—O); 4.40 (bm, 2H, HO—CH$_2$CH$_2$, CH$_2$CH$_2$—OH)

EXAMPLE 9

1,5-di(p-toluensulfonyl)oxy-2(S)-methoxy-3-oxa-pentane (F4)

1,5-dihydroxy-2(S)-methoxy-3-oxa-pentane (E4) (1.4 g, 10.3 mmole), prepared as described in Example 8, was dissolved in dry pyridine (10 ml) and treated at 0° C. with p-toluensulfonylchloride (6.4 g, 0.034 mole). The mixture was kept at 4° C. overnight, then was poured into an ice-water mixture and finally extracted with methylene chloride. The organic phase was washed with water, separated off, dried over anhydrous sodium sulphate, filtered off. The solvent was removed under reduced pressure. The crude material was chromatographed on a silicic acid column using methylene chloride as eluting agent to give 2.8 g (yield 62%) of pure title derivative, TLC on Kieselgel Plate $F_{254}$ (Merck), eluting system methylene chloride:acetone (95:5 by volume) brown spot at $R_f = 0.55$ after heating the TLC plate previously sprayed with sulforic acid.

$^1$HNMR (200 MHz, CDCl$_3$) δ: 2.44 (s, 6H, CH$_3$—Ph); 3.27 (s, 3H, OCH$_3$); 3.69 (m, 2H, SO$_2$OCH$_2$CH$_2$—O); 3.90 (m, 2H, SO$_2$OCH$_2$—CH—O); 4.11 (m, 2H, SO$_2$OCH$_2$CH$_2$—O); 4.56 (t, J=5.3 Hz, 1H, —O—CH—CH$_2$); 7.3–7.8 (m, 8H, aromatic H's).

EXAMPLE 10

Preparation of 1,5-diiodo-2(S)-methoxy-3-oxa-pentane (C4)

1,5-di(p-toluensulfonyl)oxy-2(S)-methoxy-3-oxa-pentane (F4) (1.6 g, 3.6 mmole), prepared as described in Example 9, was dissolved in methylethylketone (30 ml) and treated with sodium iodide (3.04 g, 20.2 mmole) at 85° C. for two days. After that, the solvent was removed in vacuo and the residue was added with n-hexane (50 ml) and water. The organic phase was separated off, dried over anhydrous sodium sulphate, filtered off. The solvent was removed under reduced pressure to give 1,5-diiodo-2(S)-methoxy-3-oxa-pentane (C4) (1.2 g, yield 86%). TLC on Kieselgel Plate $F_{254}$ (Merck), eluting system methylene chloride, brown spot at $R_f = 0.54$ after heating the TLC plate previously sprayed with sulforic acid.

$^1$HNMR (200 MHz, CDCl$_3$) δ: 3.15 (m, 4H, J—CH$_2$CH$_2$—OCH—CH$_2$—J); 3.40 (s, 3H, OCH$_3$); 3.80 (m, 2H, J—CH$_2$CH$_2$—O); 4.62 (t, J=5.6 Hz, 1H, O—CH—CH$_2$).

EXAMPLE 11

Preparation of 3'-deamino-[2''(S)-methoxy-4''-morpholinyl]-doxorubicin (A4)

To a solution of doxorubicin hydrochloride (80 mg, 0.138 mmole) dissolved in dry dimethylformamide (4 ml) was added 1,5-diiodo-2(S)-methoxy-3-oxa-pentane (C4, 0.8 g, 2.06 mmole) and triethylamine (0.056 ml, 0.388 mmole). The reaction mixture was kept at room temperature under stirring for 36 hrs, then was poured in water and extracted with methylene chloride. After standard work up, the crude product was purified on silicic acid column using as eluting system a mixture of methylene chloride methanol (97.5:2.5 by volume), to give, after treatment with methanolic anhydrous hydrogen chloride, 40 mg (yield 45%) of the title compound as hydrochloride salt. TLC on Kieselgel Plate $F_{254}$ (Merck), eluting system methylene chloride:methanol (19:1 by volume)

$R_f = 0.15$

Free base: $^1$HNMR (400 MHz, CDCl$_3$), δ: 13.98 (s, 1H, 6-OH); 13.27 (s, 1H, 11-OH); 8.03 (dd, J=1.1, 7.7 Hz, 1H, 1-H); 7.78 (dd, J=7.7, 8.6 Hz, 1H, 2-H); 7.39 (dd, J=1.1, 8.6 Hz, 1H, 3-H); 5.55 (m, 1H, 1'-H); 5.30 (dd, J=2.1, 4.1 Hz, 1H, 7-H); 4.74 (d, J=4.5 Hz, 14—CH$_2$OH); 4.74 (s, 1H, 9-OH); 4.49 [dd, J=2.6, 4.1 Hz, 1H, NCH$_2$—CH(OCH$_3$)O]; 4.08 (s, 3H, 4-OCH$_3$); 3.94 (q, J=6.6 Hz, 1H, 5'-H); 3.93 [m, 1H, NCH$_2$CH(H)O]; 3.67 (m, 1H, 4'-H); 3.54 [m, 1H, NCH$_2$CH(H)O]; 3.38 [s, 3H, NCH$_2$CH-OCH$_3$]; 3.27 (dd, J=19, 18.8 Hz, 1H, 10-Heq); 3.04 (d, J=18.8 Hz, 1H, 10-Hax); 3.00 (t, J=4.5 Hz, 1H, CH$_2$OH); 2.60 [dd, J=4.1, 11.4 Hz, 1H, NCH(H)CHOCH$_3$]; 2.6–2.5 (m, 3H, NCH(H)CHOCH$_3$, NCH$_2$CH$_2$O); 2.4–2.3 (m, 2H, 8-Heq, 3'-H); 2.15 (dd, J=4.1, 14.7 Hz, 8-Hax); 1.76 (m, 2H, 2'-CH$_2$); 1.26 (d, J=6.6 Hz, 3H, 3H, 5'-CH$_2$).

EXAMPLE 12

Preparation of 1,5-dihydroxy-2(R)-methoxy-3-oxa-pentane (E5)

The title compound was prepared as described in Example 8 starting from 1,5-dioxo-2(R)-methoxy-3-oxa-pentane (D5) which in turn can be prepared as described in "Methods on Carbohydrate Chemistry" Acad. Press., Vol. 1, 445, (1962). TLC on Kieselgel Plate $F_{254}$ (Merck), eluting system methylene chloride:methanol, brown spot at $R_f = 0.24$ after heating the TLC plate previously sprayed with sulforic acid.

EXAMPLE 13

Preparation of 1,5-di(p-tolueneuslonyl)oxy-2(R)-methoxy-3-oxa-pentane (F5)

1,5-dihydroxy-2(R)-methoxy-3-oxa-pentane (E5), prepared as described in Example 12, was transformed into the title compound F5 following the same procedure reported in Example 9. TLC on Kieselgel Plate $F_{254}$ (Merck), eluting system methylene chloride:acetone (95:5 by volume) brown spot at $R_f = 0.55$ after heating the TLC plate previously sprayed with sulforic acid.

EXAMPLE 14

Preparation of 1,5-diiodo-2(R)-methoxy-3-oxa-pentane (C5)

1,5-di(p-toluensulfonyl)oxy-2(R)-methoxy-3-oxa-pentane (F5), prepared as described in Example 13, was converted into the diiodo derivative C5 following the procedure described in Example 10. TLC on Kieselgel Plate F$_{254}$ (Merck), eluting methylene chloride, system brown spot at R$_f$=0.54 after heating the TLC plate previously sprayed with sulfuric acid.

EXAMPLE 15

Preparation of 3'-deamino-[2''(R)-methoxy-4''-morpholinyl]-doxorubicin (A5)

The title compound was prepared by condensing doxorubicin hydrochloride with 1,5-diiodo-2(R)-methoxy-3-oxa-pentane (C5), prepared as above described, following the procedure reported in Example 11.

TLC on Kieselgel Plate F$_{254}$ (Merck), eluting system methylene chloride:methanol (19:1 by volume) R$_f$=0.13

Free base: $^1$HNMR (400 MHz, CDCl$_3$) δ: 13.97 (s, 1H, 6-OH); 13.25 (s, 1H, 11-OH); 8.03 (dd, J=1.1, 7.7 Hz, 1H, 1-$\underline{H}$); 7.78 (dd, J=7.6, 7.7 Hz, 1H, 2-$\underline{H}$); 7.39 (dd, J=1.1, 7.6 Hz, 1H, 3-$\underline{H}$); 5.53 (d, J=3.4 $\underline{Hz}$, 1H, 1'-$\underline{H}$); 5.29 (dd, J=2.5, 4.1 $\underline{Hz}$, 1H, 7-$\underline{H}$); 4.75 (s, 2H, 14-$\underline{CH_2}$OH); 4.71 (s, 1H, 9-O$\underline{H}$); 4.46 [dd, J=2.6, 4.7 Hz, 1H, N$\underline{CH_2}$—CH(OCH$_3$)O]; 4.08 (s, 3H, 4-O$\underline{CH_3}$); 3.93 (q, J=6.6 Hz, 1H, 5'-$\underline{H}$); 3.92 [m, 1H, NCH$_2$$\underline{CH}$(H)O]; 3.70 (m, 1H, 4'-$\underline{H}$); 3.56 [m, 1H, NCH$_2$CH(H)$\underline{O}$]; 3.40 [s, 3H, NCH$_2$CH-O$\underline{CH_3}$]; 3.26 (dd, J=19, 19.9 Hz, 1H, 10-$\underline{H}$eq); 3.03 (d, J=19.9 Hz, 1H, 10-$\underline{H}$ax); 2.66 [dd, J=2.6, 11.4 Hz, 1H, N$\underline{CH}$(H)CHOCH$_3$]; 2.53 (m, 1H, N$\underline{CH}$(H)CH$_2$O); 2.5-2.3 (m, 4H, N$\underline{CH}$(H)CH$_2$O, N$\underline{CH}$(H) CHOCH$_3$, 8-$\underline{H}$eq, 3'-$\underline{H}$); 2.15 (dd, J=4.1, 14.7 Hz, 8-$\underline{H}$ax); 1.8-1.7 (m, 2H, 2'-$\underline{CH_2}$); 1.36 (d, J=6.6 Hz, 3H, 5'-$\underline{CH_3}$).

BIOLOGICAL ACTIVITY OF
3'-deamino-[2''(S)-methoxy-4''-morpholinyl]doxorubicin (A4) and
3'-deamino-[2''(R)-methoxy-4''-morpholinyl]doxorubicin (A5)

The compounds have been tested in several experimental system in order to ascertain their cytotoxicity and antitumor activity in experimental animals in comparison with parent Doxorubicin. The new anthracyclines result more cytotoxic than the parent drug on LoVo and LoVo Doxorubicin-resistant cell line (LoVo/Dx), Table 1, and are active "in vivo" against doxorubicin-resistant cell lines.

The primary screening "in vivo" was carried out in BDF1 mice bearing P388 Doxorubicin-resistant Johnson's leukemia (P388/Dx) (10$^2$ cell/mouse). The drugs were administered iv on day 1 after tumor inoculation. Results are reported in Table 2. Both compounds were active and more potent than Doxorubicin.

Compound A4 has also been tested on Doxorubicin-resistant P388 Schabel "in vitro", Table 3, and "in vivo" on BDF1 mice (10$^2$ cell/mouse), treatment iv on day 1 after the tumor inoculation, Table 4. Finally, compound Ia has been studied on solid tumor such as mammary murine and human carcinoma (MX1) with iv and oral route, Table 5 and 6.

TABLE 1

Colony assay test against LoVo and LoVo/Dx resistant cells "in vitro" (treatment for 4 hrs)

| Compound | LoVo (IC$_{50}$ = ng/ml)$^a$ | LoVo/Dx (IC$_{50}$ = ng/ml)$^a$ | R.I.$^b$ |
|---|---|---|---|
| Doxorubicin | 48.8 | 2553 | 52.6 |
| A4 | 8.7 | 31.7 | 3.6 |
| A5 | 6.5 | 40.1 | 6.1 |

$^a$IC$_{50}$ = concentration inhibiting 50% of colony growth
$^b$R.I. = Resistance Index = (IC$_{50}$ LoVo/Dx)/(IC$_{50}$ LoVo)

TABLE 2

Effect of A4 and A5 on Doxorubicin-resistant P388 Johnson's Leukemia "in vivo".

| Compound | O.D.$^c$ (mg/kg) | T/C$^d$ % |
|---|---|---|
| Doxorubicin | 13 | 86 |
| A4 | 0.09 | 250 |
| A5 | 0.13 | 244 |

$^c$O.D. = Optimal Dose: maximally tollerated dose.
$^d$T/C % = Median survival time of treated mice over median survival time of controls × 100.

TABLE 3

Effect of A4 on sensitive and Doxorubicin-resistant P388 Leukemia (Schabel) "in vitro" (treatment 1 hr).

| Compound | P388 (IC$_{50}$ ng/ml)$^e$ | P388/Dx (IC$_{50}$ ng/ml)$^e$ |
|---|---|---|
| Doxorubicin | 52.7 | 4000 |
| A4 | 7.6 | 24.3 |

$^e$IC$_{50}$ = concentration inhibiting 50% of cellular survival.

TABLE 4

Effect of A4 on Doxorubicin-resistant P38B Schabel's Leukemia "in vivo".

| Compound | O.D.$^c$ (mg/kg) | T/C$^d$ % |
|---|---|---|
| Doxorubicin | 13 | 100 |
| A4 | 0.09 | 153 |

TABLE 5

Effect of A4 on murine mammary carcinoma.

| Compound | Route and Treatment Schedule | O.D.$^c$ (mg/kg) | Tumor Inhibition % |
|---|---|---|---|
| Doxorubicin | iv q4dx4$^f$ | 5.85 | 99 |
| A4 | iv q4dx4 | 0.065 | 94 |
|    | po q4dx4$^g$ | 0.1 | 97 |

$^f$iv q4dx4 = treatment iv every four days for four times
$^g$po q4dx4 = oral treatment every four days for four times

TABLE 6

Effect of A4 on mammary human carcinoma (MX1).

| Compound | Route and Treatment Schedule | O.D.$^c$ (mg/kg) | Tumor Inhibition % |
|---|---|---|---|
| Doxorubicin | iv q7dx3$^h$ | 6 | 72 |
| A4 | iv q7dx3 | 0.05 | 98 |
|    | po q7dx3$^i$ | 0.13 | 99 |

$^h$iv q7dx3 = treatment iv every seven days for three times
$^i$po q7dx3 = oral treatment every seven days for three times

We claim:

1. A diiodo compound of the formula:

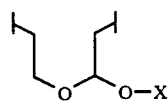
wherein X represents a linear or branched $C_1$–$C_6$ alkyl group, said diiodo compound having an (S)-configuration at the 2-position.
2. A diiodo compound of the formula:
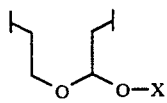
wherein X represents a linear or branched $C_1$–$C_6$ alkyl group, said diiodo compound having an (R)-configuration at the 2-position.
* * * * *

UNITED STATES PATENT AND TRADEMARK OFFICE
CERTIFICATE OF CORRECTION

PATENT NO. : 5,304,687
DATED : April 19, 1994
INVENTOR(S) : Alberto BARGIOTTI, et al.

It is certified that error appears in the above-indentified patent and that said Letters Patent is hereby corrected as shown below:

On the title page, Item [63], the Related U.S. Application Data should read as follows:

--Continuation of Ser. No. 741,539, Aug. 14, 1991, filed as PCT/EP90/02229, Dec. 18, 1990, abandoned.--

In column 1, lines 6 and 7 should read as follows:

--This application is a continuation of application Ser. No. 07/741,539, Aug. 14, 1991, filed as PCT/EP90/02229, Dec. 18, 1990, abandoned.--

Signed and Sealed this

Twenty-sixth Day of July, 1994

Attest:

BRUCE LEHMAN

Attesting Officer          Commissioner of Patents and Trademarks